US007822783B2

(12) United States Patent
Carrabis

(10) Patent No.: US 7,822,783 B2
(45) Date of Patent: *Oct. 26, 2010

(54) PROGRAMMABLE METHOD AND APPARATUS FOR REAL-TIME ADAPTATION OF PRESENTATIONS TO INDIVIDUALS

(75) Inventor: Joseph Carrabis, 49 Brighton Dr., Nashua, NH (US) 03064

(73) Assignees: Joseph Carrabis, Nashua, NH (US); Susan Carrabis, Nashua, NH (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/053,064

(22) Filed: Mar. 21, 2008

(65) Prior Publication Data

US 2008/0183318 A1 Jul. 31, 2008

Related U.S. Application Data

(63) Continuation of application No. 10/071,731, filed on Feb. 7, 2002, now Pat. No. 7,383,283.

(60) Provisional application No. 60/329,770, filed on Oct. 16, 2001.

(51) Int. Cl.
*G06F 17/30* (2006.01)

(52) U.S. Cl. ............ 707/803; 707/736; 707/758; 707/781; 707/791; 707/802; 707/809; 707/812; 707/822; 707/828; 700/100; 700/101; 700/102; 700/103; 700/104; 700/105; 700/106; 700/107; 700/108; 700/89; 700/90; 700/91; 700/92; 700/93; 700/94; 700/95; 705/10; 705/11; 705/12; 705/13; 705/14; 705/15; 340/500; 434/258; 434/236; 434/237; 434/238; 702/182; 702/183; 600/300; 273/453; 706/14; 345/957

(58) Field of Classification Search ............... 707/736, 707/758, 781, 791, 802, 803, 809, 812, 822, 707/828, 999.1, 999.101, 999.102, 999.104; 700/100–108, 89–95; 705/10–15; 340/500; 434/258, 236–238; 702/182–183; 600/300; 273/453; 706/14; 345/957
See application file for complete search history.

(56) References Cited

U.S. PATENT DOCUMENTS 5,243,517 A * 9/1993 Schmidt et al. ............ 600/544
5,682,882 A * 11/1997 Lieberman .................. 600/301

(Continued)

*Primary Examiner*—Syling Yen
(74) *Attorney, Agent, or Firm*—Hayes Soloway P.C.

(57) ABSTRACT

The present invention is a method of obtaining information regarding an individual's environment using a programmable device. The first step of the method is sensing a psychomotor behavioral element of an activity engaged by the individual. The type of activity engaged by the individual can be any sensible activity under the sun, including breathing, thinking, generating heat, etc. The next step in the inventive method is determining the preferred modalities of the individual based on the psychomotor behavioral element of the activity engaged by the individual. Provided herein are calculations used for determining the preferred modalities of the individual based on the psychomotor behavioral element of the activity. In the present context, the preferred modalities are the semi-conscious or nonconscious desires of the individual, indicated by nonconscious actions, to experience her environment in a specific manner. The information obtained by the inventive method can be used in several ways. One way to use the information obtained is by automatically altering the environment. Another way to use the information is to make the individual or other individuals aware of the nonconscious or semi-conscious interests.

16 Claims, 5 Drawing Sheets

U.S. PATENT DOCUMENTS

| | | | |
|---|---|---|---|
| 5,987,415 A * | 11/1999 | Breese et al. | 704/270 |
| 6,018,682 A * | 1/2000 | Rise | 607/45 |
| 6,230,111 B1 * | 5/2001 | Mizokawa | 702/182 |
| 6,233,545 B1 * | 5/2001 | Datig | 704/2 |
| 6,347,261 B1 * | 2/2002 | Sakaue et al. | 700/245 |
| 6,499,025 B1 * | 12/2002 | Horvitz et al. | 706/52 |
| 6,820,037 B2 * | 11/2004 | Simon | 702/182 |
| 7,107,253 B1 * | 9/2006 | Sumner et al. | 706/45 |

* cited by examiner

PROGRAMMABLE METHOD AND APPARATUS FOR REAL-TIME ADAPTATION OF PRESENTATIONS TO INDIVIDUALS

CROSS REFERENCE TO RELATED APPLICATION

This application is a continuation application of U.S. application Ser. No. 10/071,731 filed Feb. 7, 2002.

The present invention claims priority based on Provisional Application Ser. No. 60/329,770, filed Oct. 16, 2001.

FIELD OF THE INVENTION

The present invention is in the field of programmable devices. Specifically, the present invention is in the field of programmable devices for customizing an individual's environment.

BACKGROUND OF THE INVENTION

There are several technologies currently available which are designed to create more personal, efficient work and/or pleasure environments for humans. The best known technologies are listed here along with the problems inherent in them:

1—Human Computer Interaction (HCI) Design: This technology is an outgrowth of the ergonomic engineering efforts of the 1960's through 70's and functions by bringing descriptions of the audience and proposed functionality into focus. It can be broken down into: 1) describe the characteristics of the potential user population(s) via demographics, domain knowledge, etc.; 2) determine the goals the user(s) wants to accomplish; 3) identify the tasks that the users perform (in task language); 4) analyze the tasks to develop layers of sub-tasks (all of this should be in terms of tasks, not actions); 5) gather as much information as you can for design and later testing; 6) brainstorm about your user population and the relevant tasks they perform; and 7) draft a User/Task Table. Each of these stages can be broken down into detailed substages.

This technology is useful for determining characteristics of large groups only. It requires larger and larger sample populations of the desired demographic to create a model with any degree of accuracy. While not a flaw, per se, this technology is predicated on first defining a viable demographic model. This requires first defining characteristics of the demographic, said characteristics are themselves based on assumptions which may or may not be valid as they are based on observations of inconsistencies in the general population. These inconsistencies become the characteristics of the desired demographic, and so on for further refinements of the population.

2—Heuristic Design: This technology involves an on-going series of experimental, often trial-and-error, methods wherein a given design or system is continually modified based on field analysis, surveys, unsolicited feedback, etc. In most cases this technology requires users to be actively monitored or interrogated about their usage and/or activity in the subject environment. Data collected by such means is then compiled and correlated to possible design changes which are then either included or discarded based on decisions made without the continued input of the original users. Often any implemented changes are not injected into the subject environment unless some time after the original study, at which point the original users have themselves changed and the newly implemented changes are no longer relevant.

3—Bayesian Analysis: The simplest explanation of Bayesian Analysis is to say that it is statistics weighted by experience. While not useful in situations with exact binary outcomes, it is very useful in situations where not all the variables are known or defined but in which the final state of those variables is well known and defined. Its usefulness in these latter situations is based on its ability to infer preferred (ie, "experienced") final states and then determine the statistical probability of the preferred state without knowing the statistical probability of the underlying states. Thus, statistics may tell us that state 2 has a ½5 chance of being the final state of a 25 state system, but if experience tells us state 2 occurs 80% of the time, a simplified Bayesian Analysis would suggest that state 2 actually has an 80% chance of occurring again. A key element of Bayesian Analysis is that prior beliefs must be stated and well-defined because they will greatly affect the outcome of the analysis. Problems with technologies based on this method involve the requirement of prior beliefs and experience with which to weight the statistical probabilities, the accuracy and validity of these prior beliefs and experiences, there is no attempt to measure the goodness of the curve's fit to real results, and the end results of the analysis may rely more on the prior weighting measurements than the actual data itself.

4—Aggregators: The most popular of all existing technologies, Aggregators work simply by collecting as much data as possible then mining it for patterns which have ended in desired results. Typical Aggregators group people demographically (zip code is the most obvious), financially (income), by spending habits (buying patterns), and the like. All Aggregators work by determining what an individual will do based on what large groups of similarly employed, similarly housed, etc., individuals have done. The quality of the aggregate result is therefore based on larger and larger population models and the belief that "all individuals who meet this criteria behave in this way" (see Bayesian Analysis above). The problem with Aggregators is their inability to adjust to individual behaviors on the fly, to learn from immediate and near-past experience, to utilize that learning in real-time, and to evolve their methods as the populations evolve.

5—User Analysis: User Analysis is a multi-step technology which starts with a definition of purpose then moves through definition of goal or accomplishment, definition of audience, determination of strategy, determination of representative users, testing with said users, redefinition of purpose, goal or accomplishment, to creation of information and/or content. Substages include surveying potential users, interviews, task analysis, and the use of focus groups. In short, User Analysis is market analysis refined. The major problem with this technology is that the user, except in focus groups or in representational studies, has no control over the presentation or content they are delivered. In focus groups and representational studies people are in controlled and constrained environments where they are not free to be themselves and act out their inner attitudes based on whims of the moment.

6—User Centered Design: This technology tends to use the very latest behavioral and perceptual analysis tools to develop models of user behavior, often with exhaustive user testing for the ultimate in usage optimization. The "user testing" mentioned above takes the form of highly invasive methods such as having users wear hardware to monitor their brain activity, pulse, respiration, eye movement, and so on. In many ways User Centered Design is a polygraph method of determining user needs, wants and desires. Based on this kind of testing, decisions for design and implementation are made. Flaws are inherent in the description above. Design and implementation decisions are made based on controlled, constrained, contrived and confined experimentation over a large group of users in an unnatural setting. The end result of these tests are inherently invalid unless an adequate model of the unnatural setting skewing factor can be validated and taken into account.

7—Usage Analysis: This technology monitors how something is used in order to make it more usable. Usage Analysis is a combination of several of the methods already presented (Aggregator, Bayesian, HCI and User Design). User Analysis attempts to create aggregate data across as many platforms and transactions as possible. The more discrete forms of this technology rely more on Aggregation and Bayesian or similar forms of analysis rather than HCI and User Design methods. In all cases, Usage Analysis relies heavily on past usage to determine present and future usage. An example of this is using a table-knife for a screwdriver, or "necessity is the mother of invention". Because Usage Analysis would expend its efforts watching how the table-knife was used as a table-knife to make a better table-knife, no time would be spent appreciating that the basic form of the table-knife is a close approximation to the basic form of a screwdriver, hence a one-way substitution could be made. As with previously mentioned technologies, usage analysis creates a constrained environment in which analysis occurs. This constrained environment does not reveal the complete range of interactions between the user and the environment or tool being used.

SUMMARY OF THE INVENTION

The present invention results from the realization that an individual's environment can be automatically manipulated to being more consistent with preferred modalities (wherein a modality is a mode of behavior or operation) of the individual, without receiving consciously entered opinion or personal information from the individual and without the use of generalized demographic information regarding a group with whom the individual is associated, by sensing and interpreting psychomotor behavioral activity engaged in by the individual.

The premise of the present invention is to have sensing devices, many of which already exist in an individual's environment or which could be inconspicuously arranged so as not to alter the environment, sensing an individual's actions. A processing unit then interprets those actions, analyzing the psycho- and cognitive-motor behavior and other activity to identify preferred modalities of the individual. Modifiable environmental units are then modified to make the environment more consistent with the individual's preferred modalities.

One embodiment of the present invention could be used in automobiles. Pressure sensitive sensors could be located in the seat and steering wheel of a vehicle. On one occasion, an individual who becomes lost may sit forward in the seat and grip the steering wheel more tightly than normal before activating a navigational system to acquire directions. On the next occasion the individual sits forward and grips the steering wheel, the present invention would prompt the individual to acquire directions or present a map to the individual. Similarly, an individual may exhibit characteristic signs of a person about to fall asleep, sitting back in the seat, loosening the grip, etc. The present invention would recognize this event and adjust the lights, radio, or other modifiable environment units to stimulate the individual's senses and avert sleep. Production cars with voice-recognition/activation technology (Lexus, for example), already have the necessary sensory systems to implement this technology. They are merely lacking the necessary rule/inference structure. An automobile is just one of many environments for which the present invention is applicable.

The present invention solves the flaws in HCI Design technology because it creates demographics one user at a time by matching user non-conscious activity against a template of desired activity. HCI Design may create a demographic of all Jeep owners and therefore conclude that members of this demographic like Jeeps. The present invention would determine what types of customization individual members would prefer and offer these customizations to them, and recognize members who do not like Jeeps, determine which vehicle would be a better match, and move them to that new demographic, all without asking any overt questions to the individual user.

The present invention solves the flaws in Heuristic Design by allowing for immediate adaptation of the environment for ultimate usability by the user, based on current design constraints, and by being able to do so repeatedly as the user's immediate needs and desires change. Further, the information gathered by the present invention could be used to radically simplify and collapse the HD process by allowing for design changes which increase environment flexibility (allowing for more immediate adaptation to a wider audience) rather than designing to a specific audience itself. In other words, the present invention would suggest changes which allowed the environment to adapt to a wider spectrum of users rather than a wider spectrum of use.

The criticisms of Bayesian Analysis are the requirement of prior beliefs for statistical weighting, the relative subjectivity of those prior beliefs, the goodness of the resulting curve fit and that the conclusions may depend more on the validity of the prior belief weighting than on the resulting data. Challenges to Bayesian Analysis include creating rigorous definitions for the priors and deciding the complexity of the models and the probabilities to assign to them. The present invention bypasses the requirements for prior beliefs by creating its own prior belief "system" based on immediate experiential evidence. Statistical weighting does not occur until enough experiential evidence is supplied by the system (based on a business rules matrix). There is no relative subjectivity of this immediate prior belief "system" because the data is not open to interpretation except by the business rules matrix and, should there be a conflict, the ACO and ACR engines would alert the system designer to it. The ACO and ACR engines, which provide a self-learning environment for the present invention, negate the concern over creating rigorous definitions because the business rules matrix is the definition set, the business rules matrix defines the complexity of the model, and the probabilities aren't assigned until enough immediate experiential data exists to create them. Because the present invention is highly modular, complex business rule sets can be scaled and chunked until highly accurate models can be created, then the result sets from these models can be summed into the larger business rule set. In this example, the ACO and ACR engines are constantly calibrating and recalibrating the system to immediately configure the system's abilities to the user's needs.

The present invention has the ability to create populations of 1 and to adjust, learn, and evolve immediately to what that population is doing in real-time, avoiding the pitfalls of Aggregators. Further, the present invention can recognize similarities amongst these populations of 1 to create populations of many to which highly targeted business rules can apply. Where as Aggregators can only work once a sufficiently large population has been recognized, and then only work within the statistical accuracy of their model, the present invention works by creating a finite and minuscule model, learning about it, then determining if what it's learned can: 1) be applied anywhere else in its system; and 2) has appeared anywhere else in its system. In case 1, it learns how unique a unique individual is and adapts itself accordingly. In case 2, it uses what its learned elsewhere and sees if existing rule set can be applied in this situation. In all cases, it evolves through use in real-time, keeps a memory of what it's learned and evolves its knowledge-base based on new experience.

The flaws in User Analysis include that the user, except in focus groups or in representational studies, has no control over the presentation or content they are delivered. In focus groups and representational studies people are in controlled and constrained environments where they are not free to be themselves and act out their inner attitudes based on whims of the moment. The present invention makes no use of focus groups or representational studies because each individual user becomes their own focus group and representational study. Further, the present invention immediately adapts itself based on the inner attitudes and whims of the moment that individual users experience as they're engaged in an activity. There are no constraints or controls on the user's experience except what they themselves are willing to experience.

The flaws in User Centered Design are centered around the highly invasive methods of testing before final design decisions can be reached. As with User Analysis technologies, the user is often in a controlled, constrained, and highly unnatural setting when tests are performed. First, the present invention makes no use of hardware other than that which is already available at the interface. No extra hardware is used or maintained by the user or user surrogates. Second, the present invention creates user-specific design based on the immediate needs, wants and desires of the individual user as needs, wants and desires change and evolve. Lastly, the present invention works at the time the user is actively engaged in an activity in the privacy of their activity. The end result of an the present invention session involve no unnatural setting nor do they require skewing factors to determine validation because the settings are natural and their validation is based on real-time usage experience.

The present invention does much the same as Usage Analysis in that it monitors how something is used in order to make it more usable. What the present invention does that Usage Analysis does not do is discover how a tool or environment would be used and make it easier to promote that new usage pattern. Using the table-knife example, the present invention would recognize the form rather than the intended usage and bring alternative uses into play as required based upon that form. The present invention works without constrained environments and brings new uses to existing forms based on the current requirements of the user, allowing for the complete range of interactions between the user and the environment or tool being used.

DETAILED DESCRIPTION OF THE INVENTION

Figure 1:
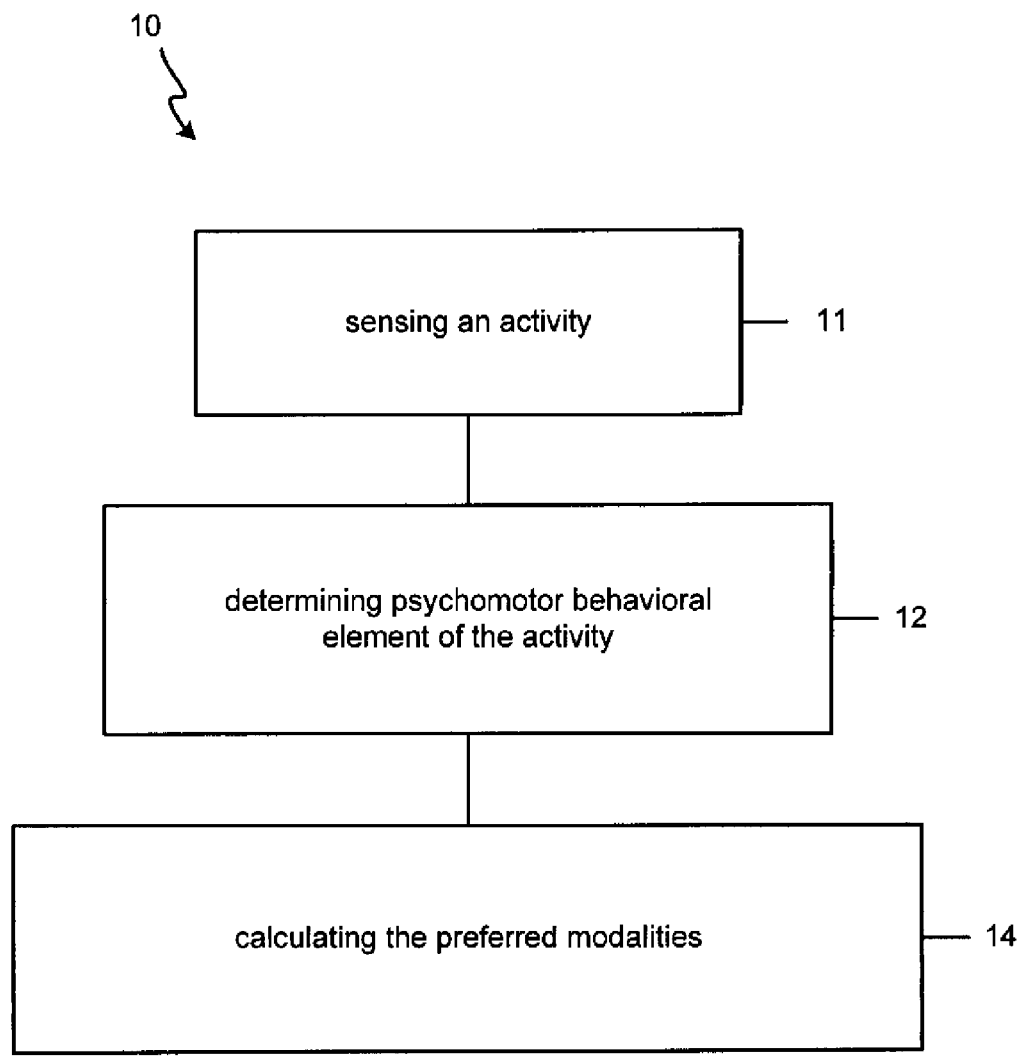
FIG. 1 is a flow diagram of the broadest embodiment of the method of the present invention.
Figure 2:
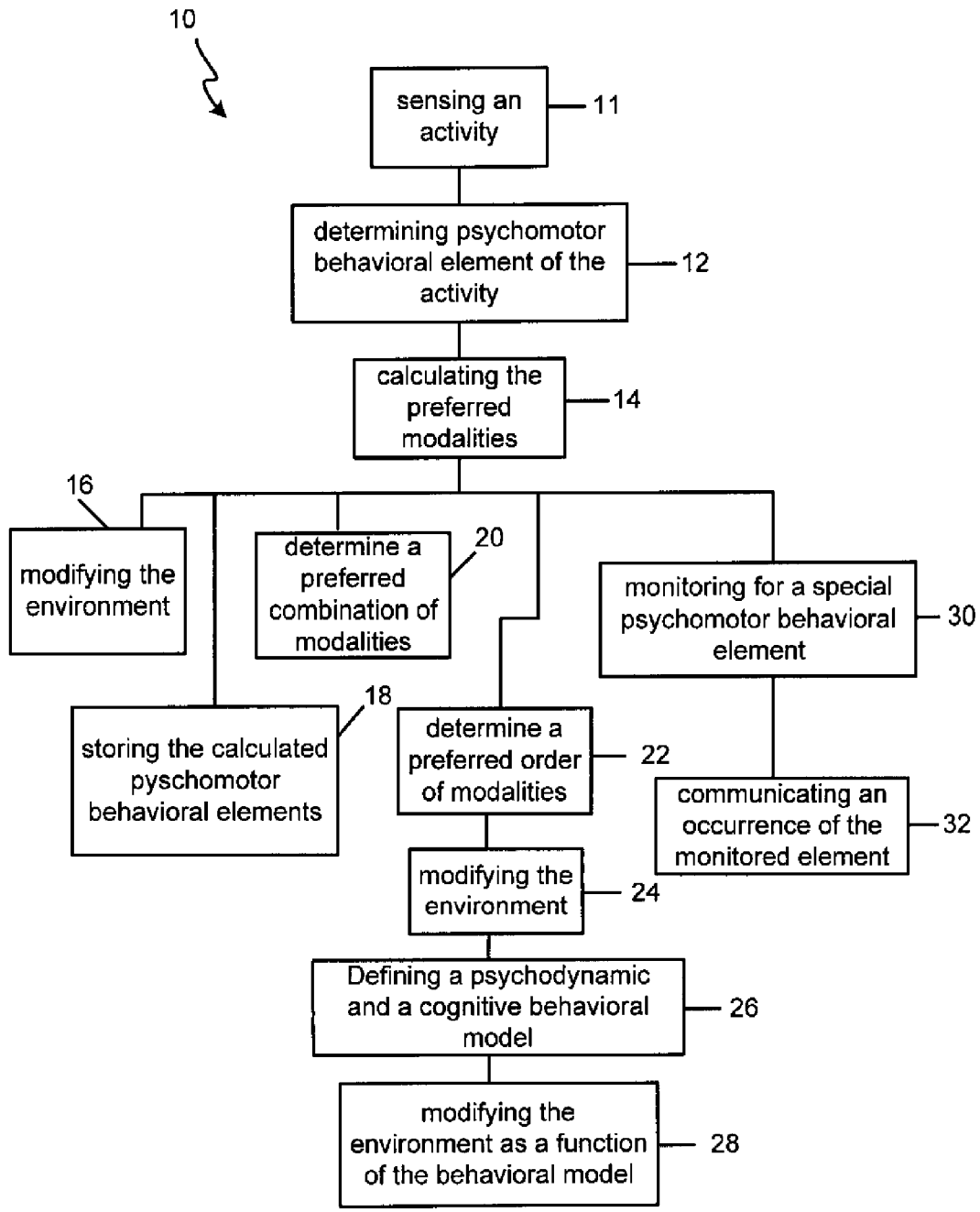
FIG. 2 is a flow diagram of another embodiment of the method of the present invention.
Figure 3:
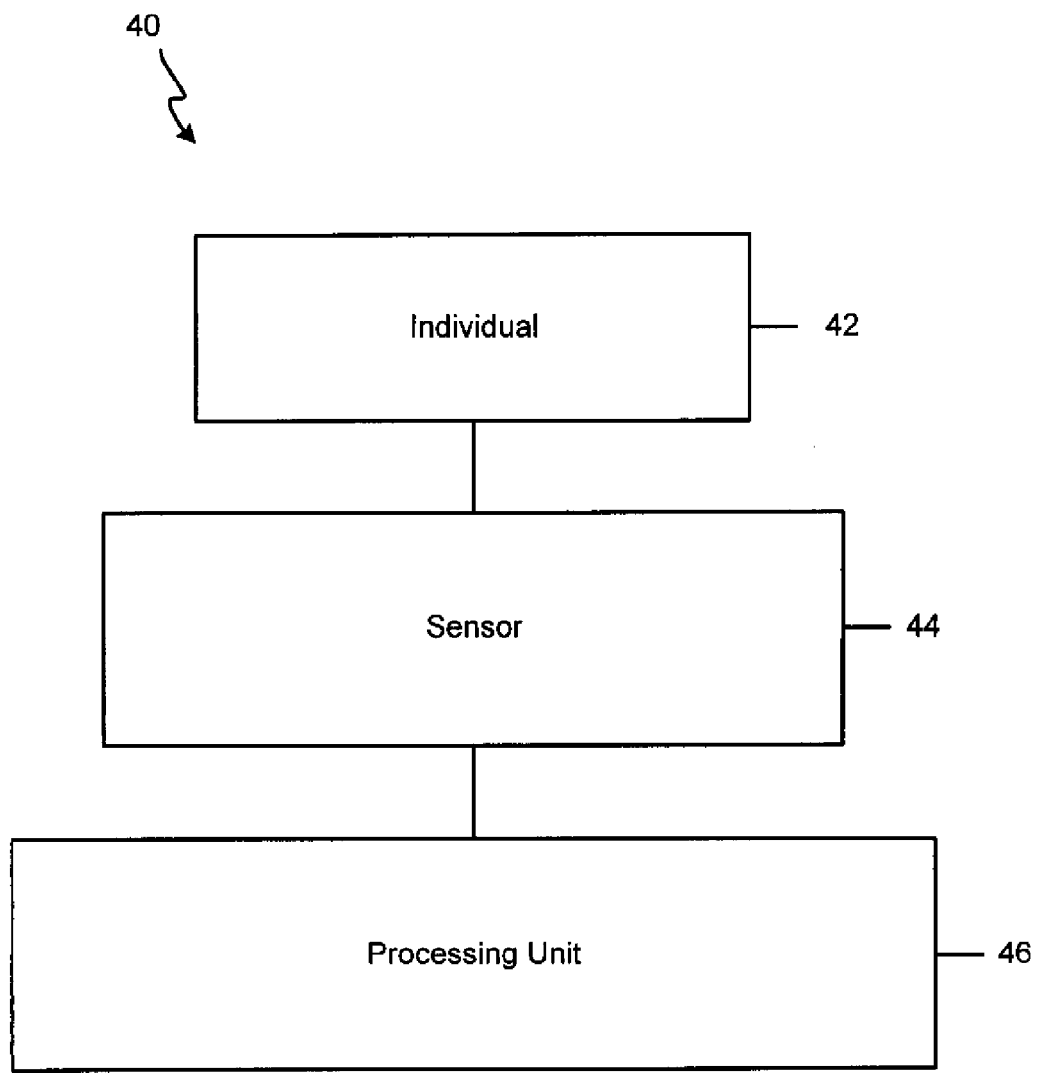
FIG. 3 is a block diagram of the broadest embodiment of the apparatus for the present invention.
Figure 4:
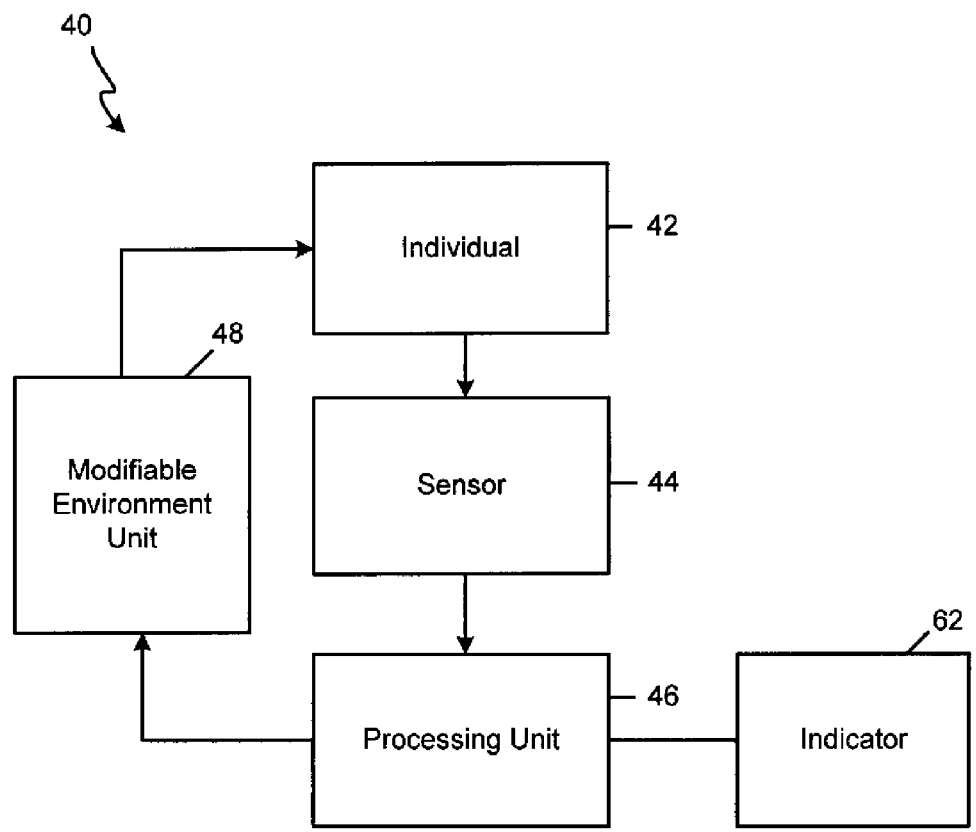
FIG. 4 is a block diagram of another embodiment of the apparatus for the present invention.
Figure 5:
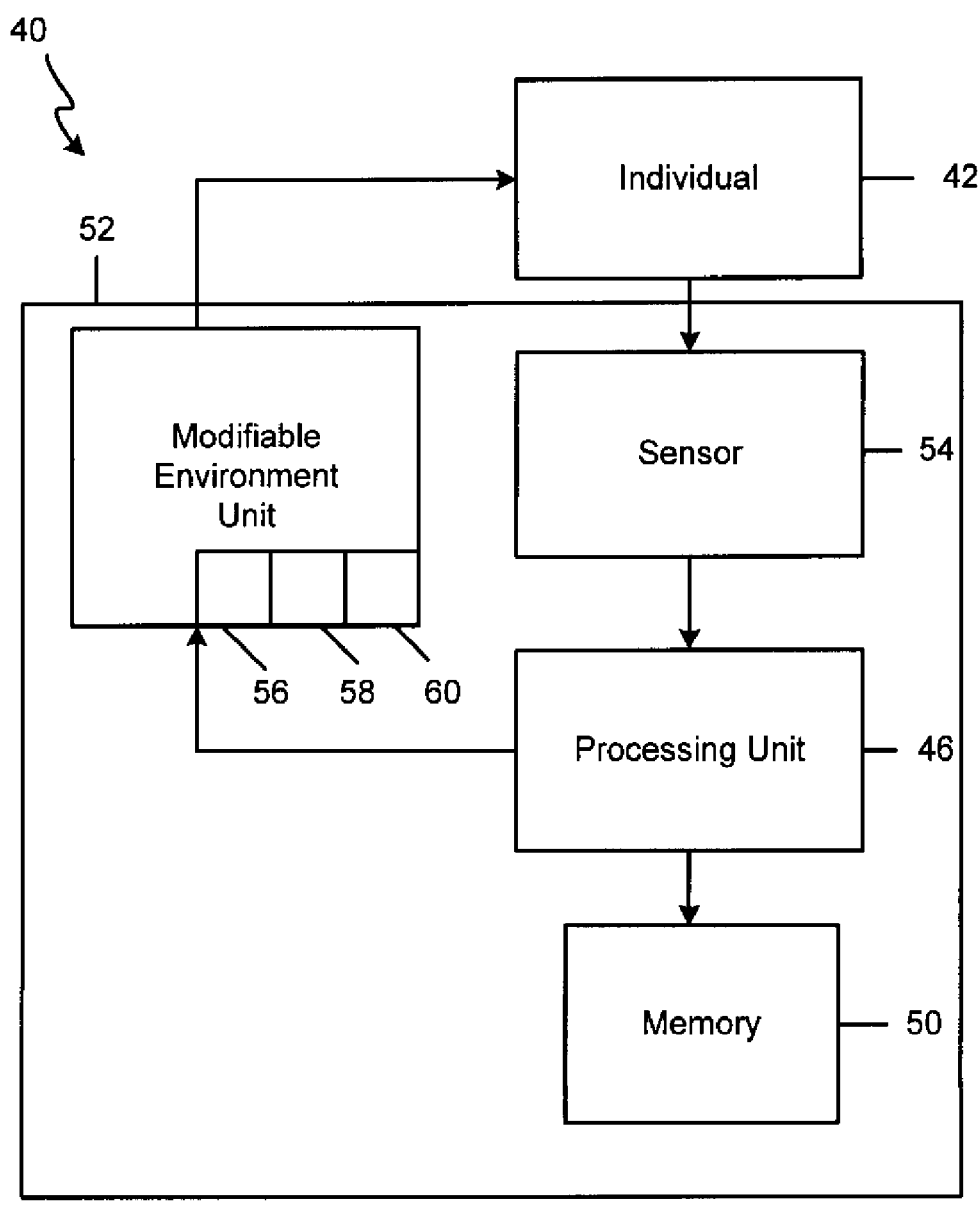
FIG. 5 is a block diagram of another embodiment of the apparatus for the present invention wherein the apparatus is part of a personal computer.

The present invention uses psychometrics, a concept related to biometrics except that the technology relates to a person's thought patterns as opposed to biological traits. The difference allows psychometrics to generate-value in applications presently addressed by biometrics as well as applications for which biometrics is too limited. Therefore the detailed description of the claimed invention is briefly prefaced with an enabling description of biometrics as it relates to one of many applications.

Psychometrics

Psychometrics relies on principles from psychomotor research. One application of the present invention combines psychometrics and the latest in web technologies to link what happens in the viewer's mind to what happens to the mouse and keyboard to what happens to the cursor to what happens on the screen. The following definitions establish the context with which to understand the present invention.

1) The person sitting at their computer, browsing a website, is the viewer.
2) The viewer is looking at websites via a browser.
3) The viewer's browser is controlling what is displayed (parts of webpages, new webpages, etc) on the computer monitor by hand motion on a pointing device called a mouse and by keystrokes on the keyboard.
4) The mouse has a symbolic representation on what is displayed via a cursor.
5) The viewer navigates the website by using the mouse to move the cursor and then clicking on an action item on the currently presented webpage.
6) Whatever is currently shown in the browser window is a single presentation from the website. This current browser window may consist of frames and other complexities but still represents a single presentation to the viewer.
7) The cursor and presentation are the interface between the viewer and the webserver which is delivering content to the browser for display.

People, regardless of cultural origin or life experience, have a psychometric tendency known as "egocentric localization." An individual's egocentric localization is their sense of where their body is positioned relative to other objects in the external environment. Thus, our viewer knows intuitively that they are sitting at their computer, knows where the computer is in relation to where they are sitting, knows where the keyboard is having only glanced at it once, knows where the mouse is having only glanced at it once, etc.

Individuals also have the ability to perceive the distances between objects within their environment. This ability is known as "object-relative localization." Object-relative localization means not only does the viewer know that they're sitting, that they are looking at their monitor to see their browser, that their hands are at or near the keyboard, and that one hand may be on the mouse from time to time, but it also means that the viewer intuitively knows the distances and spatial relationships between the monitor, the keyboard, the mouse, their seat, the top of their desk, etc.

It is important to remember that all this is being done nonconsciously.

As you read this, you are engaged in a flurry of activity of which most people are totally unaware. You are demonstrating a cognitive psychomotor process called "selective attention in vision." This means you're reading parts of this text, basically breaking the entire document into separate elements which are more easily visually digested and processed. The reason you are demonstrating selective attention in vision is because when you read, when you look at a picture, when you look at anything that requires the processing of non-remembered information, you are performing a "visual search task" and the search is for "pictoral or monocular cues" which cause your eye to tell your brain that the information your mind is seeking has been found. These concepts have a vast history in neuroscience and cognition studies.

Studies indicate that everyone projects their internal reality onto their external world. This is known as "mapping." As you read this, chances are you're making evaluations of what is written—deciding if you agree or disagree. In either case, you're taking your internal reality (the decision to agree or disagree and the thoughts that led to that decision) and projecting it onto your external world (these words as they appear in your browser or on a printed page). You're applying a part of your internal reality—what makes sense, what's valid, what you're willing to accept as true—and using it as a test for some stimulus in your external world—the information being offered herein.

When you take action based on some projection of your internal reality onto your external world, you've demonstrated a "cognitive-motor map." The "map" part we explained above. The "motor" part comes from the action taken. The "cognitive" part comes from the decision you made after doing some information processing. All of these parts deal with "eye movement and information processing." Eye movement and information processing are closely related because one can not happen without the other. Even someone staring off into space thinking is nonconsciously performing minute contractions of the eye muscles as thoughts slide into and out of place.

Because human beings are wired the way they are, your body tracks where your eyes are looking. Unless we're being coy or trying to see something with peripheral vision, we tend to "face things head on." This is especially true when we're searching for something (as in "visual search task"). We "face tasks head on" because it allows us to bring the full implementation of our cognitive-motor maps to bear on the problem; both eyes are focusing on the target, the ears are equidistant and our auditory system is focused, even our hands tend to go into acquisitional behavior (you're ready to reach for something). When using the computer our hands normally do not come off the keyboard or the mouse until we are done processing and begin evaluating (mapping). Then, at some point, our hands go back to where they were . . . almost. For example, moving your hands from mouse to keyboard or vice-versa. This action indicates that some non-conscious decision was made to operate differently in the environment.

Because people all over the world are physiologically wired substantially similarly, people all over the world have "sensory motor learning" experiences. As a child learns to catch a ball, they get bopped by the ball a few times before they learn to co-ordinate what their eye sees with what their hands do. Sensory motor learning is necessary because normal perceptual development depends upon active bodily movement under higher sensory (visual, auditory, kinesthetic) guidance. But there are two aspects to sensory motor learning. The aspect of motor learning that occurs watching TV or going to the theater is called "exafference." Exafference is stimulation that acts upon a passive observer. The second aspect of motor learning involves more "audience involvement" and is called "reafference." Reafference is stimulation that changes as a result of an individual's own movements . . . like moving your mouse or using your keyboard to alter the interface which appears in your browser.

Finally, the "stimulus control and attention" concept tells us that an individual's attention tends to focus where that individual is able to control the amount of stimulus given. When you work on a car, you want a good light to see what you are doing. You focus the light in the area of the car you are working to see better. And, of course, the light allowed you to focus your attention on a certain part of the car, bringing it into better visual focus than the other parts in the car.

So you're sitting at your computer, using your browser performing a visual search task and something in the presentation provides a pictorial or monocular cue that causes your brain to suspend eye movement which signals your mind to alter the information processing it's doing briefly because whatever this pictorial or monocular cue was, your brain needed to control the amount of stimulus in order to focus your attention. These actions are where sensory motor learning and reafference come in because you focused your attention by using the mouse or keyboard to move the cursor or enter some data (a command, text, etc) to whatever caught your attention. These actions were all happening nonconsciously.

Even if you tied your hands so that they could only come free when you were ready to request the next presentation, your sensory motor system knows where your attention was and won't rest until it's done its job and made some part of your body make some kind of movement in the cue's direction (even when there's more than one cue being processed). The movement may be minute, but it'll happen unless you have tremendous physical training and control. So your eyes go where your mind was and your hands are sure to follow. Or in this case, the cursor will follow.

Psycho-, socio-, and neuro-linguistics teach that at the highest level, everybody has the same maps because everybody has the same set of sensory apparatus. These same three disciplines teach that as you go deeper and deeper, everybody's maps change to the point where you can tell from a single sentence much about an individual's life and state of mind.

As described herein, people project their internal reality externally. This projection helps us know who we are, our boundaries, our limits, our friends and our neighbors. When we are a viewer sitting at a browser, we project our internal reality onto the presentation in the browser window.

When the viewer projects their internal reality onto the presentation, they are looking for something to connect to, something which is familiar at some level and to which they can use as a reference for everything else on the screen. Individuals do this in the real world via the sense of egocentric localization. Individuals do this in the virtual world by using the cursor and the brain's abilities to recognize patterns and discriminate familiar patterns from less familiar ones. In a very real sense, the cursor takes the place of our hand. Thus, an individual's "virtual" egocentric location is referenced by the cursor's position on the screen.

Just as virtual egocentric localization occurs when an individual finds out where the cursor is within the presentation, object-relative localization occurs when the individual determines where everything else is on the screen in relation to the cursor.

Once the viewer finds out where everything is on the screen via a quick glance, they start parsing. It doesn't matter if they are reading text or looking at pictures, the viewer will parse the presentation into easily processable pieces of information. This especially occurs if the viewer wants to remember the information.

To be clear, people don't "read" webpages as they "read" a book. Usually they scan and when scanning they tend to use a stimulus control to focus their attention on what they're reading because there's so much visual noise on the page they can't focus otherwise. Stimulus control is the individual in the guise of the cursor. On the computer, we control stimulus via the mouse and keyboard. Specifically, parsing the presentation requires an individual's body to match their selective attention in vision to selective movement in the body due to sensory-motor learning and reafference. In other words, where the eyes go, the cursor will follow.

Humans have as many modalities as they have senses. For the purposes of a simplified discussion, we use a simplified web browser interface for reference.[1] We can match the sensory modalities to the presentation via a grid. The grid represents three of the many sensory modalities most humans share; visual, auditory and kinesthetic. As web bandwidth increases more modalities can be added. For now, this is enough.

[1] A simplified version for a web interface matches sensory modalities to the presentation via a grid as explained in the main text. A true implementation calibrates the user's modalities to their psycho- and cognitive-motor cues and behavior regardless of their activity on the presentation. In other words, someone might never move their mouse from the lower left hand corner of the web presentation. The simplified system would determine the user had modalities A and B. The true system would recognize that this corner of the screen was to be mapped via a Fixed Point Theorem to the entire presentation and calibrate for modalities accordingly.

The viewer is sitting at their browser looking at a presentation. When a pictorial or monocular cue occurs, and if their hand is on the mouse or keyboard, the cursor will move minutely if not grossly (in the sense of motor movement) towards that cue.

There is a definite distance associated with the movement of the cursor from where it started to where it ended up. Before the viewer clicks on anything, the viewer is merely attempting to focus their attention by controlling the stimulus. Because the presentation is basically a two dimensional grid, the path the cursor takes, which is governed by the viewer's mouse movement, can be measured as:

$$f(distance)=Dx+Dy$$

There is more than just linear distance associated with moving the cursor. Forcing the viewer to visually search for pictorial or monocular cues on a presentation is highly desirable because doing so takes time. When we add time to the simple equation above we get something more like this:

$$f(movement)=(Dx/Dt)+(Dy/Dt)$$

Also, a path isn't a simple (X1−X0)+(Y1−Y0) distance. A path, like a path in the woods, means avoiding things, going around others, taking the best route possible when the egocentric localizing viewer determines what's around in the object-relative localizing way.

Even though the actual mouse motions may have been minute, the viewer was parsing that interface to focus attention. Therefore, the equation more resembles:

$$f(\text{sensory motor activity})=\Sigma_t((dx/dt)+(dy/dt))$$

But the sensory-motor activity is tied to the cognitive-motor map because the brain (cognitive) is telling the body (motor) what to do based on what the eyes are telling it (sensory). Specifically, the brain is doing lots of work to direct attention to what the mind wants to know and it's doing it along sensory modality channels, so the equation is really:

$$\int_x\int_y\int_t(\text{attention})\partial x\partial y\partial t=\int_x\int_y\int_t(\Sigma(\text{sensory modality})f(\text{modality})(\partial x/\partial t)+\Sigma(\text{sensory modality})f(\text{modality})(\partial y/\partial t)+\Sigma(\text{sensory modality})f(\text{modality})(\partial t/\partial t))\partial x\partial y\partial t$$

The best part about this equation is that the Σ(sensory modality)f(modality) parts—which relate to the visual, auditory and kinesthetic sensory modalities—of the above equation are fairly well known and have been documented for about the past 25 years. Also be aware that these equations are the reduced form of the general technology equation $$f(\text{attention})=_{j=1}\Gamma^\infty(\Sigma_1 f(\text{modality}_i)(\delta j/\delta t))\cdot_{j=1}\Gamma^n(\delta j/\delta t)(d^n i/dt^n) \ ||j=\text{dimension counter, i=modality counter}$$

which accounts for any environment and any number of degrees of freedom within that environment (the behavioral form of this equation is given later in this document).

Psychometrics Applied

The science surrounding psychomotor behaviors has been developing for some time. However, the application of the science to electronic devices is new. As individuals continue to become more digital, more interactive with programmable apparatus, the concept of tracking an individual's psychomotor behaviors using those same programmable apparatus becomes increasingly convenient.

Given software which can track cursor movement through time (meaning velocity and acceleration, relative position and distancing), a string of variables can be sent back to the webserver. This string of variables can contain a string of (X,Y,T) triplets decoded by server-side software to determine movement through the grid and time in each quadrant (the quadrants can be increasingly small as presentation needs dictate). When grid movement is determined the modality summations can be selected to determine if the viewer's attention is focused on visual, auditory, kinesthetic or other related cues.

Based on the results of this equation, the webserver can prepare in real time what the next presentation and interface should be in order to capture more of the viewer's attention by presenting the web content in modalities which the viewer has nonconsciously selected. Thus content is directed via a smart webserver to a viewer based on the viewer's nonconscious selection.

One of the goal's of this invention is to make the brain work as little as possible because its primary job in an environment is to stop the mind from processing information in order to focus attention. The present invention gives the brain increasingly little to do so that the mind is totally engaged and receiving all the information we care to give it in ways it wants to receive it. Technically, this is the foundation for hypnosis and, within reason, that's what the present invention does.

Returning to a previously discussed equation:

$$f(movement)=(Dx/Dt)+(Dy/Dt)$$

Movement is the measure of cursor movement over the presentation. From any starting point on a presentation, the cursor movement is a series of ordered doublets, ((X,T), (Y,T)), where X and Y represent distance along an Cartesian grid and T is the time of each movement. There are several software packages and languages which monitor cursor movement over a presentation for the purposes of popups and the like, and there are several methods of moving the cursor other than with the mouse. All of these methods are commonly available over the internet and do not constitute a unique part of this invention.

Each presentation sent by the present system carries a set of specific meta-tags. One of these meta-tags acts as a session-id. Each presentation itself is mapped to an interface grid. This grid exists solely in the scripting language of the invention.

The interface grid has a series of reference targets. These reference targets allow the system to know where the original cursor position was on each presentation by determining Dx and Dy via cursor movement before crossing any reference target.

It has been demonstrated that the complexity of any presentation system can be determined by the equation:

$$1/\alpha + 1/\beta + 1/\gamma = 1$$

where $\alpha$, $\beta$ and $\gamma$ represent the complexity of the presentation format, the web server and the data server respectively.[2] Each of these variables can be tiered so that the above equation can represent a very large web system. It was also demonstrated that it is possible to atomize any presentation so that the most minute changes in the presentation can be managed by a sufficiently designed server system.

[2] The use of web server, data server, etc., are for the simplified discussion of a web system. The true system and the equations given are part of an Information Driven Presentation Architecture.

When a viewer requests a presentation through the present invention, they are sent an instantiation, which is a unique presentation (except in the case of a home page for an unknown viewer). The web server system also sends the instantiation to the engine. The instantiation also contains the viewer identification. As the viewer moves about the presentation, their interface collects ((x,t), (y,t)) doublets and sends them back to the engine at some interval which is determined from the above equation. The engine uses these doublets and the present instantiation as data for the equations, which allows the engine to determine a viewer's modalities and attention.

As more intelligence is gathered regarding individual viewer preferences, the engine sends instructions to the web server system to build a highly customized instantiation. When the viewer has finished with the instantiation and selects an action item from the interface, the engine has already built the instantiation inside the web server and delivers it. Likewise for additional instantiations until this viewer session is complete. This is but one means of using a simple web browser interface as the environmental focus. Other means of using web browsers as the environmental focus or the use of other types of environments may similarly be realized.

The present invention is a method 10 of obtaining information regarding an environment for an individual using a programmable device. The first step of the method is sensing 12 a psychomotor behavioral element of an activity engaged by the individual. The type of activity engaged by the individual can be any sensible activity under the sun, including breathing, thinking, generating heat, etc. Every activity has some psychomotor behavioral element, breathing heavier or pacing when nervous or excited, generating excess heat when embarrassed, sitting back when relaxing, sitting forward when interested, etc. The next step in the inventive method 10 is determining 14 the preferred modalities of the individual based on the psychomotor behavioral element of the activity engaged by the individual. Provided herein are calculations used for determining 14 the preferred modalities of the individual based on the psychomotor behavioral element of the activity. In the present context, the preferred modalities are the conscious or nonconscious desires of the individual to experience her environment in a specific manner. The information obtained by the inventive method 10 can be used in several ways.

One application of the inventive method 10 includes modifying 16 at least one modifiable environmental unit to at least partially conform to the preferred modalities. The present application of the inventive method 10 could involve modifying 16 a computer presentation to provide more of an audio presentation and less text. The present application of the inventive method 10 could also involve modifying 16 the environment by providing a map to a driver whose psychomotor behavioral activity indicates she is lost. Another example of the present application of the inventive method 10 could involve modifying 16 the light level in an office based on the psychomotor behavioral elements of the activity of the office worker to increase the sensed 12 productivity over time. A narrower embodiment of the present application involves modifying 16 the environment unit in real-time.

Another narrow embodiment of the inventive method 10 involves storing 18 the sensed 12 psychomotor behavioral element in a user history. Developing a user history can further enable determining 14 preferred modalities based on past and present sensed 12 psychomotor behavioral elements. One method of storing 18 the sensed psychomotor behavioral element is storing 18 in terms of preferred representational geometries via linear algebraic transforms.

Another narrow embodiment of the inventive method 10 narrows the step of determining preferred modalities to further determine 20 a preferred combination of modalities and 22 an ordering of modalities by preference thereby further defining a focus of the individual's preferred modalities. The present inventive method 10 may determine 14 that the individual prefers to receive information audially as opposed to visually. This narrower embodiment would further determine 20 the individual prefers to receive information audially 65% and visually 35%. This narrower embodiment would further determine 22 the individual prefers to receive information in the aforementioned percentages by receiving 50% of the visual information first and then receiving 100% of the audile information, before finishing the information presentation with the remaining 50% of the visual information. These determinations 20 and 22 can be made by using the equation:

$$\Sigma \int_{-\infty}^{\infty} ((\Sigma G_i(\delta x_i/\delta_i t))/(\Sigma G_i(dx_i/dt_i))) dG_i dt_i \propto \Psi(G)$$

where G≡a matrix equation which takes the form $$\Pi(m_1, m_2, m_3, \ldots, m_n)$$

$$x_1, x_2, x_3, \ldots, x_n$$

$$y_1, y_2, y_3, \ldots, y_n$$

$$t_1, t_2, t_3, \ldots, t_n$$

This formula matches the psychomotor behavior, as demonstrated by the individual's activity, against a well established map of psychoneurologic structures in the brain. In essence, it determines which parts of the brain are active, hence what the mind is doing consciously and non-consciously, based on what conscious and non-conscious behavioral elements demonstrated with the individual's activity. This formula utilizes a spatial mapping system and does a time-spatial analysis to coordinate activity with neural processing.

This narrower embodiment can be further narrowed by adding the step of modifying 24 the environmental unit to provide content in the environment in the preferred combination of modalities and the preferred order of modalities. In this further narrowed embodiment, the combination and the order are placed in at least one respective co-ordinate group of representational geometry to which focus of the individual is drawn, as indicated by the psychomotor behavioral element.

The narrower embodiment is also narrowed by adding two additional steps to the inventive method 10. The first additional step is defining 26 a psychodynamic and a cognitive behavioral model using the preferred combination of modalities and the order of modalities. The second additional step is modifying 28 at least one environmental unit as a function of the psychodynamic behavioral model and the cognitive behavioral model.

Next, the present inventive method 10 can be narrowed by requiring that the environment is multi-dimensional and the environment has a plurality of modifiable environmental units.

Finally, another application of the present inventive method 10 involves two additional steps for taking advantage of the information obtained. The first step is preprogramming 30 the device to monitor the individual for at least one specific type of psychomotor behavioral element. The second step is communicating 32 an occurrence of the specific type of psychomotor behavioral element. The present application could be used in a vehicle wherein the device is preprogrammed 30 to monitor for psychomotor behavioral elements indicative of the driver falling asleep and communicates 32 to the driver that she should pull the vehicle over until driver overcomes her drowsiness. The present application could also be used for a lie detector test wherein a voice recorder preprogrammed 30 to monitor stress in a voice and communicate 32 whether the person recorded is telling the truth. The present application could also be used for security by preprogramming 30 a device to monitor psychomotor behavioral elements of activity in relation to a user history of psychomotor behavioral elements and if the elements are sufficiently different, communicating 32 to an emergency number that the device has determined an irregular user—possibly an auto theft or unauthorized computer user depending on the ultimate use of the application.

The present invention is also a programmable apparatus 40 for obtaining information regarding an environment with respect to an individual 42 having preferred modalities. The apparatus 40 includes at least one sensor 44 for sensing psychomotor behavioral activity of the individual 42. The apparatus 40 also includes a processing unit 46 connected to the sensor 44 for receiving the sensed psychomotor behavioral activity and calculating the individual's preferred modalities based on the sensed psychomotor behavioral activity. Once the present information is received and calculated, there are many applications for using the information.

A narrower embodiment of the programmable apparatus 40 further includes at least one modifiable environmental unit 48, modified by at least one instruction from the processing unit 46 to at least partially conform the environment to the calculated preferred modality of the individual 42.

Another narrower embodiment of the programmable apparatus 40 further includes a memory device 50 to store sensed psychomotor behavioral activity of the individual 42. A narrower embodiment of this embodiment involves using stored sensed psychomotor behavioral activity of the individual 42 in the memory device 50 to refine the preferred modality calculation.

Another embodiment of the inventive apparatus 40 involves having the preferred modalities calculated while the sensors 42 operate while concurrently using the sensed psychomotor behavioral activity for modifications to the environmental units 48.

Another embodiment of the apparatus 40 involves a personal computer 52, wherein the sensor 42 includes at least one input device 54 for the computer and the modifiable environmental unit 48 includes at least one output device 56, such as a visual display 58 or speaker 60. In this embodiment, the processing unit 46 would determine preferred modalities based on psychomotor behavioral activity using the input device 54 and not conscious decision-making by the individual 42.

Finally, another embodiment of the apparatus 40 uses an indicator 62 connected to the processing unit 46, wherein the processing unit 46 is preprogrammed to monitor for specific psychomotor behavioral activity. In this embodiment, the indicator 62 indicates when a match occurs between the specific psychomotor behavioral activity and the sensed activity and/or when a match fails to occur. This embodiment enables the apparatus 40 to be used as a lie detector, security measure or other similar application, as previously described herein.

Prevarication (lie detection) is done by monitoring whether the individual is using parts of the brain which create information or retrieve information. For example, when asked a direct question about a past event and the individual's brain activity indicates increased usage of the parts of the brain which create data, it's a good guess that the person is fabricating information about the past event rather than recalling it. Information regarding cognitive- and psycho-motor activity during prevarication is well documented in the literature on psycho- and neuro-linguistics. The human-machine interface monitors these various motor activities and the equations listed in this invention determines which parts of the brain are in use based on the monitored activity.

Security systems (such as "Intrusion Detection") are performed by a piece of the invention called the "Memetic Engine and Drivers". These components determine the memetic equivalents of someone's thoughts while they're performing some function. While the outward action of the function (logging into a system, starting a car, signing a name) involve the same motor skills they don't involve the same psycho- or cognitive-motor processes. The human-machine interface monitors these motor processes and the equations described in this invention determine the base thought processes, or memes, which make up the activity.

I claim:

1. A method of obtaining information regarding an environment for an individual, having preferred modalities and engaged in activity, using a programmable device, said method comprising the steps of:

sensing at least one psychomotor behavioral element of the activity engaged by the individual; and determining a preferred combination of modalities and an ordering of modalities by preference of the individual based on the psychomotor behavioral element of the activity engaged by the individual, and wherein the combination and order of modalities is calculated by an equation: $\Sigma \int_{-\infty}^{\infty} ((\Sigma G_i(\delta x_i/\delta_i t))/(\Sigma G_i(dx_i/dt_i)))dG_i dt_i \propto \Psi(G)$.

2. The method of claim 1 further comprising modifying at least one modifiable environmental unit to at least partially conform to the preferred modalities.

3. The method of claim 2 wherein the environment unit is modified in real-time.

4. The method of claim 1 further comprising storing the sensed psychomotor behavioral element in a user history.

5. The method of claim 4 wherein the sensed psychomotor behavioral element is stored in terms of preferred representational geometries via linear algebraic transforms.

6. The method of claim 1 further comprising the step of modifying the environmental unit to provide content in the environment in the preferred combination of modalities and the order of modalities by preference whereby the combination and the order are placed in at least one respective co-ordinate group of representational geometry to which attention of the individual is drawn, as indicated by the psychomotor behavioral element.

7. The method of claim 1 further comprising:
defining a psychodynamic and a cognitive behavioral model using the preferred combination of modalities and the order of modalities; and
modifying at least one environmental unit as a function of the psychodynamic behavioral model and the cognitive behavioral model.

8. The method of claim 1 wherein the environment is multi-dimensional and has a plurality of modifiable environmental units.

9. The method of claim 1 further comprising
preprogramming the device to monitor the individual for at least one specific types of psychomotor behavioral elements; and
communicating an occurrence of the specific type of psychomotor behavioral element.

10. A programmable apparatus for obtaining information regarding an environment to an individual having preferred modalities, said apparatus comprising:
at least one sensor for sensing psychomotor behavioral activity of the individual; and
a processing unit connected to the sensor for receiving the sensed psychomotor behavioral activity and calculating the individual's preferred modalities based on the sensed psychomotor behavioral activity, wherein the processing unit determines a preferred combination of modalities and an ordering of modalities by preference thereby further defining a focus of the individual's attention, and wherein the processing unit utilizes an equation: $\Sigma \int_{-\infty}^{\infty} ((\Sigma G_i(\delta x_i/\delta_i t))/(\Sigma G_i(dx_i/dt_i)))dG_i dt_i \propto \Psi(G)$ to determine the combination and order of modalities.

11. The apparatus of claim 10 further comprising at least one modifiable environmental unit, modified by at least one instruction from the processing unit to at least partially conform the environment to the calculated preferred modality of the individual.

12. The apparatus of claim 10 further comprising a memory device to store sensed psychomotor behavioral activity of the individual.

13. The apparatus of claim 12 wherein the processing unit uses stored sensed psychomotor behavioral activity of the individual to refine the preferred modality calculation.

14. The apparatus of claim 11 wherein the preferred modalities are calculated while sensing psychomotor behavioral activity and concurrently used for modifications to the environmental units.

15. The apparatus of claim 11 wherein the sensor includes at least one input device for a computer and the modifiable environmental unit includes at least one output device.

16. The apparatus of claim 10 further comprising an indicator connected to the processing unit, wherein the processing unit is preprogrammed to monitor for specific psychomotor behavioral activity and the indicator indicates at least one of the group consisting of:
a match between the sensed psychomotor behavioral activity and the specific psychomotor behavioral activity; and
a nonmatch between the sensed psychomotor behavioral activity and the specific psychomotor behavioral activity.

* * * * *